United States Patent
Lee et al.

(10) Patent No.: US 10,314,876 B2
(45) Date of Patent: *Jun. 11, 2019

(54) METHOD FOR TREATING DIABETES MELLITUS CAUSED BY PANCREATITIS

(71) Applicant: Chen-Yu Lee, Taipei (TW)

(72) Inventors: Chen-Yu Lee, Taipei (TW); Yan-Chih Liao, Taipei (TW)

(73) Assignee: Chen-Yu Lee, Taipei (TW)

(*) Notice: Subject to any disclaimer, the term of this patent is extended or adjusted under 35 U.S.C. 154(b) by 18 days.

This patent is subject to a terminal disclaimer.

(21) Appl. No.: 15/642,561

(22) Filed: Jul. 6, 2017

(65) Prior Publication Data

US 2019/0008915 A1 Jan. 10, 2019

(51) Int. Cl.

| | | |
|---|---|---|
| *A61K 35/618* | (2015.01) | |
| *A61K 36/8945* | (2006.01) | |
| *A61K 35/32* | (2015.01) | |
| *A61K 33/26* | (2006.01) | |
| *A61K 36/21* | (2006.01) | |
| *A61K 36/65* | (2006.01) | |
| *A61K 36/64* | (2006.01) | |
| *A61K 36/14* | (2006.01) | |
| *A61K 36/718* | (2006.01) | |
| *A61K 36/605* | (2006.01) | |
| *A61K 36/708* | (2006.01) | |
| *A61K 36/12* | (2006.01) | |
| *A61K 36/35* | (2006.01) | |
| *A61K 36/804* | (2006.01) | |
| *A61K 36/11* | (2006.01) | |

(52) U.S. Cl.
CPC .......... *A61K 36/8945* (2013.01); *A61K 33/26* (2013.01); *A61K 35/32* (2013.01); *A61K 35/618* (2013.01); *A61K 36/11* (2013.01); *A61K 36/12* (2013.01); *A61K 36/14* (2013.01); *A61K 36/21* (2013.01); *A61K 36/35* (2013.01); *A61K 36/605* (2013.01); *A61K 36/64* (2013.01); *A61K 36/65* (2013.01); *A61K 36/708* (2013.01); *A61K 36/718* (2013.01); *A61K 36/804* (2013.01)

(58) Field of Classification Search
None
See application file for complete search history.

(56) References Cited

U.S. PATENT DOCUMENTS

2015/0238542 A1* 8/2015 Kim ............... A61K 35/618
424/547
2017/0197891 A1* 7/2017 Huang ............. C05G 3/02

OTHER PUBLICATIONS

Chen-Yu Lee et al., "Integrated TCM and Western Medicine Efficacy in the Treatment of Diabetic Encephalopathy", Dec. 2016, vol. 4, No. 1, pp. 9-33.

* cited by examiner

*Primary Examiner* — Ralph J Gitomer
(74) *Attorney, Agent, or Firm* — Bacon & Thomas, PLLC

(57) ABSTRACT

A therapeutic method for treating diabetes mellitus, particularly diabetes caused by pancreatitis, comprising administering an effective amount of a Chinese herbal medicine to a subject. The Chinese herbal medicine is an extract of a mixture comprising specific amount of raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptidis Rhizoma, cortex Mori, rhubarb (*Rhei Radix* et *Rhizoma*), and Davallia formosana (*Davallia formosana* Hay.).

10 Claims, No Drawings

METHOD FOR TREATING DIABETES MELLITUS CAUSED BY PANCREATITIS

BACKGROUND OF THE INVENTION

1. Field of the Invention

The present invention relates to a therapeutic method for treating diabetes mellitus, more particularly a method for treating diabetes caused by pancreatitis

2. Description of Related Art

As the potential of Chinese herbal medicine for treating cancer, Chinese herbal medicine has drawn public's attention in recent years. The principle of Chinese herbal medicine application is based on the practice of traditional Chinese medicine theory.

Diabetes is a metabolic disease, the typical characteristic is long-term high blood sugar and difficult to drop back to normal level. Diabetes also leads to a variety of symptoms or complications, including polyphagia, polydipsia, polyuria, blurred vision, headache, muscle weakness, slow wound healing, cardiovascular disease, stroke, chronic kidney disease, diabetic foot, and retinopathy.

There is no effective medicine can completely cure diabetes mellitus at the moment. Treatments normally recommended such as taking drugs for lowering blood sugar, improving lifestyle and dietary habits, and weight loss can only improve symptoms.

Diabetes is divided into type 1 diabetes, type 2 diabetes, and other types of diabetes according to different causes, and pancreatitis is also one of the causes of diabetes. Since there is no single drug can treat all types of diabetes, there is a need to treat diabetes based on different causes. Therefore, it is necessary to develop medicines or methods for treating diabetes caused by pancreatitis.

SUMMARY OF THE INVENTION

The object of the present invention is to provide a method for treating diabetes caused by pancreatitis using Chinese herbal medicine. To achieve the object, the present invention provides a method for treating diabetes caused by pancreatitis, comprising administering a Chinese herbal medicine to a subject in need.

The Chinese herbal medicine of the present invention is an extract of a first mixture comprising raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.).

In a preferred embodiment of the present invention, the Chinese herbal medicine is prepared by the following steps: providing raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) to form the first mixture; mixing the first mixture with water to obtain a second mixture; decocting the second mixture to obtain a crude extract; and filtering the crude extract to remove a residue and obtain the Chinese herbal medicine.

In a preferred embodiment of the present invention, the Chinese herbal medicine is the extract of the first mixture comprising 4-6 parts by weight of raw oyster shell powder, 4-6 parts by weight of raw Os Draconis, 7-9 parts by weight of Haematitum (Hematite), 2-4 parts by weight of Magnetitum (Magnetite), 4-6 parts by weight of radix Achyranthis Bidentatae (*Achyranthes bidentata*), 4-6 parts by weight of rhizoma Dioscoreae (*Dioscoreae Rhizoma*), 4-6 parts by weight of radix Paeoniae Rubra (*Paeoniae Radix Rubra*), 4-6 parts by weight of radix Rehmanniae (*Rehmannia*), 3-5 parts by weight of semen Platycladi (*Platycladi Semen*), 7-19 parts by weight of Coptis Rhizome (*Coptidis Rhizoma*), 7-21 parts by weight of Mori Cortex, 0.1-2 parts by weight of Rhubarb (*Rhei Radix* et *Rhizoma*), and 3-11 parts by weight of Davallia formosana (*Davallia formosana* Hay.).

In a preferred embodiment of the present invention, the part by weight of the first mixture is 3.75 grams per part.

In a preferred embodiment of the present invention, the first mixture further comprises Dipsacus japonicus (*Dipsaci Radix*).

In a preferred embodiment of the present invention, the first mixture further comprises 3-5 parts by weight of Dipsacus japonicus (*Dipsaci Radix*).

In a preferred embodiment of the present invention, blood sugar or blood lipid in the subject in need is lowered.

In one preferred embodiment of the present invention, blood sugar in the subject in need is lowered.

In a preferred embodiment of the present invention, the Chinese herbal medicine is administered via oral administration, enteral administration, or intravenous injection.

In a preferred embodiment of the present invention, the Chinese herbal medicine further comprises a pharmaceutically acceptable carrier, a stabilizer, a diluent, a dispersant, a suspending agent, a thickening agent, an excipient, or the combination thereof.

The novel technical features of the present invention, including specific features, are disclosed in the scope of claims. Other objects, advantages, and novel features of the invention will become more apparent from the following detailed description.

DETAILED DESCRIPTION OF THE PREFERRED EMBODIMENT

Medical or Pharmaceutical Terms

Unless specified otherwise, all technical and scientific terms set forth in the specification and claims of the present invention are defined as follows. The singular terms "a", "an" and, "the", unless specified otherwise, can refer to more than one object. Unless specified otherwise, conventional techniques employed in the embodiments of the present invention include high performance liquid chromatography (HPLC), protein chemistry, biochemistry, recombinant DNA technology, and pharmacological techniques. The terms "or" and "and" used herein, unless specified otherwise, refer to "and/or". In addition, the terms "include" and "comprise" used herein are open ended conjunctions. The preceding paragraphs are merely systematic reference and should not be construed as limiting the subject matter of the invention. Unless specified otherwise, the materials used herein are commercially available, and the ways to get materials listed below are merely exemplary.

The term "diabetes caused by pancreatitis" used herein refers to a diabetic disease or symptom caused by pancreatitis, wherein "pancreatitis" may be acute or chronic pancreatitis.

The terms "carrier" and "excipient" used herein refer to a compound or agent that does not interfere with the therapeutic effect and has functions of assisting in drug delivery and assisting the cell or tissue to absorb the drug.

The term "diluent" used herein refers to a compound or agent for diluting a drug prior to administration; a diluent may be used to stabilize the compound or drug and provide a more stable administration state and environment.

The aforementioned additives may be aromatics, buffers, binders, colorants, disintegrants, diluents, emulsifiers, extenders, flavor-improving agents, gellants, glidants, preservatives, skin-penetration enhancers, solubilizers, stabilizers, dispersions, suspending agents, sweeteners, tonicity agents, viscosity-increasing agents, or a combination thereof.

The term "pharmaceutically acceptable" used herein refers to compounds, materials, compositions, and/or dosage forms used in a reasonable medical range suitable for contacting the tissue of a subject without excessive toxicity, irritation, allergic reaction, complications, or other problems.

The term "effective amount" or "therapeutically effective amount" used herein refers to an amount of a compound or agent sufficient to relieve one or more of the symptoms of disease or condition to some degree; the result thereof can be reduction and/or alleviation of the signs, symptoms, or causes of a disease, or any other desired alteration of a biological system. For example, an "effective amount" for therapeutic uses is the amount of the Chinese herbal medicine as disclosed herein required to provide a clinically significant decrease in disease symptoms. An appropriate "effective" amount in any individual case may be determined using techniques, such as a dose escalation study.

The term "enhance", "enhancing" or the like used herein refers to increasing or prolonging the potency or duration of a desired effect. Therefore, when it comes to enhancing the effect of therapeutic agents, the term "enhancing" refers to increasing or prolonging the potency or duration of the therapeutic agents.

The term "treat", "treatment", "treating" or the like used herein refers to alleviating, abating or ameliorating at least one symptom of a disease or condition, preventing disease progression, inhibiting the disease or condition, e.g., arresting the development of the disease or condition, relieving the disease or condition, causing regression of the disease or condition, relieving the condition caused by the disease or condition, or reducing the sign or symptoms of the disease or condition either prophylactically and/or therapeutically.

Embodiments of the present invention are exemplary, and the variation of the large amount of suggested value is not abnormal due to the great variation of the individual treatment course. The dosage may vary according to individual differences, and is not limited to the activity of the drug, the treatment of the disease or physiological state, the method of administration, the individual needs, the severity of the disease, and the judgment of the physician.

General Consideration for Combination Treatments

The term "combination treatment" or the like used herein refers to administering at least one selected pharmaceuticals to a patient, further comprising a regimen, via the same or different routes simultaneously, concurrently or sequentially.

In general, the composition and other ingredients of agents do not need to be administered in the same pharmaceutical composition regarding the combination treatment illustrated and used in the embodiment. In one embodiment, it can be administered via different routes at different time due to different physical and chemical properties. In one embodiment, the initial administration is conducted according to established administration procedure, and changed by the physician on the basis of drug efficacy, dose, the mode of administration, the frequency of administration and the like.

In the embodiments of the present invention, the therapeutically effective dose varies according to the combination treatment. The combination treatment can further comprise periodic treatment, which refers to a plurality of initiation and discontinuation treatments to benefit the clinical management of the patient. The dosage of combination treatment and the coadministered compound of the present invention vary according to different factors including coadministered drugs, main therapeutic drugs, diseases, physiological abnormalities, physiological conditions and the like.

The term "composition" used herein refers to a product, the product comes from a mixture or combination of more than one active ingredients, and the active ingredients of the product is a composition of a combination drug or non-combination drug. The term "fixed combination" used herein means that the active ingredients and the co-agents are in one medication and administered simultaneously. The term "non-fixed combination" used herein refers that the active ingredients and the co-agent are in separate medication and administered simultaneously, separately, or sequentially, and there is no limitation about the administration interval. Said administration provides the subject an effective amount of a plurality compounds in the body, wherein the non-composition may be used in cocktail therapy, namely administer three or more than three active ingredients to a subject.

The dosage forms of Chinese herbal medicine used herein include, but are not limited to, solution, emulsion, suspension, powder, tablet, pill, lozenge, troche, chewing gum, capsule, and other similar or suitable dosage forms.

The present invention provides a method for treating diabetes caused by pancreatitis, comprising administering a therapeutically effective amount of Chinese herbal medicine to a subject in need; wherein the Chinese herbal medicine is an extract of a first mixture comprising raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.).

In one embodiment, the present invention provides a method for treating diabetes caused by pancreatitis, wherein the Chinese herbal medicine may be administered with another pharmaceutical composition simultaneously. In one preferred embodiment, the Chinese herbal medicine and the pharmaceutical composition may be administered simultaneously, separately, or sequentially.

The present invention includes improving complications, comorbidities, metabolic disorders, or pathological conditions of diabetes, including but not limited to, diabetes caused by pancreatitis, beta-cell gene deficiency, diabetic ketosis, atherosclerosis, cardiovascular disease, hyperglycemia, hypertension, dyslipidemia, obesity, acute or chronic renal failure, retinopathy, diabetic foot, insulin resistance, albumin blood Disease, hyperuricemia, edema, impaired glucose tolerance. In particular, the present invention includes the improvement of pancreatic inflammatory diabetes.

Materials and Preparation of Chinese Herbal Medicine

Chinese Herbal Medicine 1

The Chinese herbal medicine 1 of the present invention comprised an extract of a first mixture formed by mixing the following materials: 5 parts by weight of raw oyster shell powder, 5 parts by weight of raw Os Draconis, 8 parts by weight of Haematitum (Hematite), 3 parts by weight of Magnetitum (Magnetite), 5 parts by weight of radix Achyranthis Bidentatae (*Achyranthes bidentata*), 5 parts by weight of rhizoma Dioscoreae (*Dioscoreae Rhizoma*), 5 parts by weight of radix Paeoniae Rubra (*Paeoniae Radix Rubra*), 5 parts by weight of radix Rehmanniae (*Rehmannia*), 4 parts by weight of semen Platycladi (*Platycladi Semen*), 8 parts by weight of Coptis Rhizome (*Coptidis Rhizoma*), 8 parts by weight of Mori Cortex, 0.5 parts by weight of Rhubarb (*Rhei Radix* et *Rhizoma*), and 4 parts by weight of Davallia formosana (*Davallia formosana* Hay.); wherein it was a daily dose of the Chinese herbal medicine 1 when the part by weight of the first mixture is 3.75 g per part.

Raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) were provided in a suitable solvent for decoction; wherein raw oyster shell powder, raw Os Draconis, Haematitum (Hematite), and Magnetitum (Magnetite) were powdery substances, while radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) might be optionally pulverized before the decoction to achieve the optimum decoction effect. The suitable solvent might be water, ethanol, DMSO, or a mixture thereof.

In one preferred embodiment of the present invention, a second mixture was formed by mixing the 1600 c.c. of water with a daily dose of each ingredient of the first mixture; the second mixture was decocted at 100-120° C. for 1 hour and then filtered to remove a residue to obtain about 450 c.c. of the Chinese herbal medicine 1, and the daily dose of the Chinese herbal medicine 1 was divided into aliquots for ter in die administration.

Further, the aforementioned preparation steps of Chinese herbal medicine 1 might further comprise the following steps to achieve concentration: after filtering the residue, the extract was provided at 50-60° C. and 20-40 torr to obtain a concentrated solution through concentration and lowering pressure. Preferably, the volume of the concentrated solution was 1/14 of the original extract.

Further, an appropriate amount of corn starch (excipient) might be added into the concentrated solution to form a past, and the amount of corn starch depended on the stability of the concentrated solution. The paste might be made to be a granular drug through spray-drying.

Chinese Herbal Medicine 2

The Chinese herbal medicine 2 of the present invention comprised an extract of a first mixture formed by mixing the following materials: 5 parts by weight of raw oyster shell powder, 5 parts by weight of raw Os Draconis, 8 parts by weight of Haematitum (Hematite), 3 parts by weight of Magnetitum (Magnetite), 5 parts by weight of radix Achyranthis Bidentatae (*Achyranthes bidentata*), 5 parts by weight of rhizoma Dioscoreae (*Dioscoreae Rhizoma*), 5 parts by weight of radix Paeoniae Rubra (*Paeoniae Radix Rubra*), 5 parts by weight of radix Rehmanniae (*Rehmannia*), 4 parts by weight of semen Platycladi (*Platycladi Semen*), 18 parts by weight of Coptis Rhizome (*Coptidis Rhizoma*), 20 parts by weight of Mori Cortex, 1 parts by weight of Rhubarb (*Rhei Radix* et *Rhizoma*), and 10 parts by weight of Davallia formosana (*Davallia formosana* Hay.); wherein it was a daily dose of the Chinese herbal medicine 2 when the part by weight of the first mixture was 3.75 g per part.

Raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) were provided in a suitable solvent for decoction; wherein raw oyster shell powder, raw Os Draconis, Haematitum (Hematite), and Magnetitum (Magnetite) were powdery substances, while radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) might be optionally pulverized before the decoction to achieve the optimum decoction effect. The suitable solvent might be water, ethanol, DMSO, or a mixture thereof.

In one preferred embodiment of the present invention, a second mixture was formed by mixing the 1600 c.c. of water with a daily dose of each ingredient of the first mixture; the second mixture was decocted at 100-120° C. for 1 hour and then filtered to remove a residue to obtain about 450 c.c. of the Chinese herbal medicine 2, and the daily dose of the Chinese herbal medicine 2 was divided into aliquots for ter in die administration.

Further, the aforementioned preparation steps of Chinese herbal medicine 2 might further comprise the following steps to achieve concentration: after filtering the residue, the extract was provided at 50-60° C. and 20-40 torr to obtain a concentrated solution through concentration and lowering pressure. Preferably, the volume of the concentrated solution was 1/14 of the original extract.

Further, an appropriate amount of corn starch (excipient) might be added into the concentrated solution to form a past, and the amount of corn starch depended on the stability of the concentrated solution. The paste might be made to be a granular drug through spray-drying.

Chinese Herbal Medicine 3

The Chinese herbal medicine 3 of the present invention comprised an extract of a first mixture formed by mixing the following materials: 5 parts by weight of raw oyster shell powder, 5 parts by weight of raw Os Draconis, 8 parts by weight of Haematitum (Hematite), 3 parts by weight of Magnetitum (Magnetite), 5 parts by weight of radix Achyranthis Bidentatae (*Achyranthes bidentata*), 5 parts by weight of rhizoma Dioscoreae (*Dioscoreae Rhizoma*), 5 parts by weight of radix Paeoniae Rubra (*Paeoniae Radix*

Rubra), 5 parts by weight of radix Rehmanniae (*Rehmannia*), 4 parts by weight of semen Platycladi (*Platycladi Semen*), 15 parts by weight of Coptis Rhizome (*Coptidis Rhizoma*), 15 parts by weight of Mori Cortex, 1 parts by weight of Rhubarb (*Rhei Radix* et *Rhizoma*), and 6 parts by weight of Davallia formosana (*Davallia formosana* Hay.); wherein it was a daily dose of the Chinese herbal medicine when the part by weight of the first mixture was 3.75 g per part.

Raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) were provided in a suitable solvent for decoction; wherein raw oyster shell powder, raw Os Draconis, Haematitum (Hematite), and Magnetitum (Magnetite) were powdery substances, while radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) might be optionally pulverized before the decoction to achieve the optimum decoction effect. The suitable solvent may be water, ethanol, DMSO, or a mixture thereof.

In one preferred embodiment of the present invention, a second mixture was formed by mixing the 1600 c.c. of water with a daily dose of each ingredient of the first mixture; the second mixture was decocted at 100-120° C. for 1 hour and then filtered to remove a residue to obtain about 450 c.c. of the Chinese herbal medicine 3, and the daily dose of the Chinese herbal medicine 3 was divided into aliquots for ter in die administration.

Further, the aforementioned preparation steps of Chinese herbal medicine 3 might further comprise the following steps to achieve concentration: after filtering the residue, the extract was provided at 50-60° C. and 20-40 torr to obtain a concentrated solution through concentration and lowering pressure. Preferably, the volume of the concentrated solution was 1/14 of the original extract.

Further, an appropriate amount of corn starch (excipient) might be added into the concentrated solution to form a past, and the amount of corn starch depended on the stability of the concentrated solution. The paste might be made to be a granular drug through spray-drying.

Chinese Herbal Medicine 4

The Chinese herbal medicine 4 of the present invention comprised an extract of a first mixture formed by mixing the following materials: 5 parts by weight of raw oyster shell powder, 5 parts by weight of raw Os Draconis, 8 parts by weight of Haematitum (Hematite), 3 parts by weight of Magnetitum (Magnetite), 5 parts by weight of radix Achyranthis Bidentatae (*Achyranthes bidentata*), 5 parts by weight of rhizoma Dioscoreae (*Dioscoreae Rhizoma*), 5 parts by weight of radix Paeoniae Rubra (*Paeoniae Radix Rubra*), 5 parts by weight of radix Rehmanniae (*Rehmannia*), 4 parts by weight of semen Platycladi (*Platycladi Semen*), 18 parts by weight of Coptis Rhizome (*Coptidis Rhizoma*), 20 parts by weight of Mori Cortex, 1 parts by weight of Rhubarb (*Rhei Radix* et *Rhizoma*), 10 parts by weight of Davallia formosana (*Davallia formosana* Hay.), and 4 parts by weight of Dipsacus asper Wall; wherein it was a daily dose of the Chinese herbal medicine when the part by weight of the first mixture was 3.75 g per part.

Raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) were provided in a suitable solvent for decoction; wherein raw oyster shell powder, raw Os Draconis, Haematitum (Hematite), and Magnetitum (Magnetite) were powdery substances, while radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) might be optionally pulverized before the decoction to achieve the optimum decoction effect. The suitable solvent might be water, ethanol, DMSO, or a mixture thereof.

In one preferred embodiment of the present invention, a second mixture was formed by mixing the 1600 c.c. of water with the daily dose of each ingredient of the first mixture; the second mixture was decocted at 100-120° C. for 1 hour and then filtered to remove a residue to obtain about 450 c.c. of the Chinese herbal medicine 4, and the daily dose of the Chinese herbal medicine 4 was divided into aliquots for ter in die administration.

Further, the aforementioned preparation steps of Chinese herbal medicine 4 might further comprise the following steps to achieve concentration: after filtering the residue, the extract was provided at 50-60° C. and 20-40 torr to obtain a concentrated solution through concentration and lowering pressure. Preferably, the volume of the concentrated solution was 1/14 of the original extract.

Further, an appropriate amount of corn starch (excipient) might be added into the concentrated solution to form a past, and the amount of corn starch depended on the stability of the concentrated solution. The paste might be made to be a granular drug through spray-drying.

Example 1—Patient 1

In Example 1, a diagnosis of a patient with diabetes showed that the value of fasting blood glucose (GLU-AC) was 362, hemoglobin A1C (HBA1C) was 12.4, total cholesterol (T Chole) was 357, triglyceride (T.G.) was 352, cancer antigen 19-9 (CA 19-9) was 54.37, and tissue polypeptide antigen (T.P.A) was 117. Since values of patient's fasting blood glucose, total cholesterol, triglyceride, and pancreatic tumor markers (T.G. and T.P.A) were higher than normal level, the patient's pancreas was inflamed, swollen, or hypertrophic so that the brain gave orders to repair islet cells leading to diabetes.

The treatment given to the patient in Example 1 comprised administering the aforementioned daily dose of the Chinese herbal medicine 1 every day for 19 consecutive days; specifically, the daily dose of the Chinese herbal medicine 1 was divided into aliquots for ter in die administration.

After administration of Chinese herbal medicine 1 for 19 consecutive days (1 dose per day), the patient's GLU-AC lowered to about 118, HBA1C lowered to about 11.6, T Chole lowered to about 321, and T.G. lowered to about 277.

The Chinese herbal medicine provided by the present invention can achieve the object of improving diabetes and lowering blood lipid.

Example 2—Patient 2

In Example 2, a diagnosis of a patient with diabetes showed that the value of fasting blood glucose (GLU-AC) was 142, hemoglobin A1C (HBA1C) was 11.9, total cholesterol (T Chole) was 335, triglyceride (T.G.) was 306, cancer antigen 19-9 (CA 19-9) was 47.23, and tissue polypeptide antigen (T.P.A) was 106.3. Since values of patient's fasting blood glucose, total cholesterol, triglyceride, and pancreatic tumor markers (T.G. and T.P.A) were higher than normal level, the patient's pancreas was inflamed, swollen, or hypertrophic so that the brain gave orders to repair islet cells leading to diabetes.

The treatment given to the patient in Example 2 comprised administering the aforementioned daily dose of the Chinese herbal medicine 2 every day for 70 consecutive days; specifically, the daily dose of the Chinese herbal medicine 2 was divided into aliquots for ter in die administration.

After administration of Chinese herbal medicine 2 for 70 consecutive days (1 dose per day), the patient's GLU-AC lowered to about 112, HBA1C lowered to about 7.8, T Chole lowered to about 196, and T.G. lowered to about 135. The Chinese herbal medicine provided by the present invention can achieve the object of improving diabetes and lowering blood lipid.

Example 3—Patient 3

In Example 3, a diagnosis result of a patient with diabetes showed that the value of fasting blood glucose (GLU-AC) was 225, hemoglobin A1C (HBA1C) was 12.3, total cholesterol (T Chole) was 349, triglyceride (T.G.) was 336, cancer antigen 19-9 (CA 19-9) was 52, and tissue polypeptide antigen (T.P.A) was 113.3. Since values of patient's fasting blood glucose, total cholesterol, triglyceride, and pancreatic tumor markers (T.G. and T.P.A) were higher than normal level, the patient's pancreas was inflamed, swollen, orhypertrophic so that the brain gave orders to repair islet cells leading to diabetes.

The treatment given to the patient in Example 3 comprised administering the aforementioned daily dose of the Chinese herbal medicine 3 every day for 35 consecutive days; specifically, the daily dose of the Chinese herbal medicine 3 was divided into aliquots for ter in die administration.

After administration of Chinese herbal medicine 3 for 35 consecutive days (1 dose per day), the patient's GLU-AC lowered to about between 123 and 124, HBA1C lowered to about 10.4, T Chole lowered to about 279, and T.G. lowered to about 190. The Chinese herbal medicine provided by the present invention can achieve the object of improving diabetes and lowering blood lipid.

Example 4—Patient 4

In Example 4, a diagnosis result of a patient with diabetes showed that the value of fasting blood glucose (GLU-AC) was 128, hemoglobin A1C (HBA1C) was 10.2, total cholesterol (T Chole) was 252, triglyceride (T.G.) was 133, cancer antigen 19-9 (CA 19-9) was 23, and tissue polypeptide antigen (T.P.A) was 68.7. Since values of patient's fasting blood glucose, total cholesterol, triglyceride, and pancreatic tumor markers (T.G. and T.P.A) were higher than normal level, the patient's pancreas was inflamed, swollen, or hypertrophic so that the brain gave orders to repair islet cells leading to diabetes.

The treatment given to the patient in Example 4 comprised administering the aforementioned daily dose of the Chinese herbal medicine 4 every day for 42 consecutive days; specifically, the daily dose of the Chinese herbal medicine 4 was divided into aliquots for ter in die administration.

After administration of Chinese herbal medicine 4 for 42 consecutive days (1 dose per day), the patient's GLU-AC lowered to about 89, HBA1C lowered to about 7.4, T Chole lowered to about 190, and T.G. lowered to about 128. The Chinese herbal medicine provided by the present invention can achieve the object of improving diabetes and lowering blood lipid.

Although the present invention has been explained in relation to its preferred embodiment, it is to be understood that many other possible modifications and variations can be made without departing from the spirit and scope of the invention as hereinafter claimed.

What is claimed is:

1. A method for treating diabetes mellitus caused by pancreatitis, comprising: administering a therapeutically effective amount of a Chinese herbal medicine to a subject in need thereof,
   wherein the Chinese herbal medicine is an extract of a first mixture comprising 4-6 parts by weight of raw oyster shell powder, 4-6 pairs by weight of raw Os Draconis, 7-9 parts by weight of Haematitum (Hematite), 2-4 parts by weight of Magnetitum (Magnetite), 4-6 parts by weight of radix Achyranthis Bidentatae (*Achyranthes bidentata*), 4-6 parts by weight of rhizoma Dioscoreae (*Dioscoreae Rhizoma*), 4-6 parts by weight of radix Paeoniae Rubra (*Paeoniae Radix Rubra*), 4-6 parts by weight of radix Rehmanniae (*Rehmannia*), 3-5 parts by weight of semen Platycladi (*Platycladi Semen*), 7-19 parts by weight of Coptis Rhizome (*Coptidis Rhizoma*), 7-2 parts by weight of Mori Cortex, 0.1-2 parts by weight of Rhubarb (*Rhei Radix* et *Rhizoma*), and 3-11 parts by weight of Davallia formosana (*Davallia formosana* Hay.).

2. The method as claimed in claim 1, wherein the Chinese herbal medicine is prepared by the following steps:
   providing raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), semen Platycladi (*Platycladi Semen*), Coptis Rhizome (*Coptidis Rhizoma*), Mori Cortex, Rhubarb (*Rhei Radix* et *Rhizoma*), and Davallia formosana (*Davallia formosana* Hay.) to form the first mixture;
   mixing the first mixture with water to obtain a second mixture;
   decocting the second mixture to obtain a crude extract; and
   filtering the crude extract to remove a residue and obtain a filtrate which is the Chinese herbal medicine.

3. The method as claimed in claim 1, wherein the part by weight of the first mixture is 3.75 grams per part.

4. The method as claimed in claim 1, wherein the first mixture further comprises Dipsacus japonicus (*Dipsaci Radix*).

5. The method as claimed in claim 1, wherein the first mixture further comprises 3-5 parts by weight of Dipsacus japonicus (*Dipsaci Radix*).

6. The method as claimed in claim 5, wherein the part by weight of the first mixture is 3.75 grams per part.

7. The method as claimed in claim 1, wherein blood sugar or blood lipid in the subject in need is lowered.

8. The method as claimed in claim 1, wherein the blood sugar in the subject in need is lowered.

9. The method as claimed in claim 1, wherein the Chinese herbal medicine is administered via oral administration, enteral administration, or intravenous injection.

10. The method as claimed in claim 1, wherein the Chinese herbal medicine further comprises a pharmaceutically acceptable carrier, a stabilizer, a diluent, a dispersant, a suspending agent, a thickening agent, an excipient, or the combination thereof.

* * * * *